United States Patent
Kaji et al.

(10) Patent No.: US 9,060,807 B2
(45) Date of Patent: Jun. 23, 2015

(54) LIGHT MARKER FOR INDWELT USE IN PATIENT'S BODY AND FOR IDENTIFICATION OF LESIONS INSIDE PATIENTS TUBULAR ORGAN USING THE LIGHT MARKER

(75) Inventors: Kunihide Kaji, Tokyo (JP); Shinji Hatta, Tokyo (JP); Keita Suzuki, Tokyo (JP); Yuichi Morizane, Tokyo (JP); Toshiyuki Takara, Saitama (JP); Tatsuya Saito, Tokyo (JP); Takeshi Takigawa, Tokyo (JP)

(73) Assignee: OLYMPUS CORPORATION (JP)

( * ) Notice: Subject to any disclaimer, the term of this patent is extended or adjusted under 35 U.S.C. 154(b) by 0 days.

(21) Appl. No.: 13/042,858

(22) Filed: Mar. 8, 2011

(65) Prior Publication Data

US 2011/0160577 A1  Jun. 30, 2011

Related U.S. Application Data

(63) Continuation of application No. 11/052,575, filed on Feb. 7, 2005, now Pat. No. 7,953,473.

(30) Foreign Application Priority Data

Feb. 6, 2004 (JP) ................. 2004-030509

(51) Int. Cl.
*A61B 5/06* (2006.01)
*A61B 19/00* (2006.01)

(52) U.S. Cl.
CPC . *A61B 19/54* (2013.01); *A61B 5/06* (2013.01); *A61B 19/5202* (2013.01);

(Continued)

(58) Field of Classification Search
CPC ...... A61B 5/06; A61B 19/54; A61B 19/5202; A61B 2019/5433; A61B 2019/5441; A61B 2019/5445; A61B 2019/5408
USPC ................... 600/431, 433, 473, 478
See application file for complete search history.

(56) References Cited

U.S. PATENT DOCUMENTS 4,790,329 A * 12/1988 Simon ............................ 600/562
5,517,997 A *  5/1996 Fontenot ....................... 600/473

(Continued)

OTHER PUBLICATIONS

Search Report issued by European Patent Office and received by applicant on Dec. 13, 2011 in connection with corresponding EP patent application No. EP 05 752 924.

(Continued)

*Primary Examiner* — Long V Le
*Assistant Examiner* — Angela M Hoffa
(74) *Attorney, Agent, or Firm* — Ostrolenk Faber LLP

(57) ABSTRACT

A lesion identification system for surgical operations has a light marker adapted for placement in the vicinity of a lesion inside an organ of an organism, and a location-identifying device detecting a light emitted from the light marker at an outside of the organ for identifying a location of the lesion. The marker includes a light emitter and an engagement member associated with the emitter to be engageable with a wall of the organ. The engagement member includes a clip. The light emitter emits light with a wavelength in a near-infrared range. The device includes an endoscope comprising an inserter section having an image pickup element picking up a reflected light, involving the light from the light marker, at an outside of the organ, and an image pickup unit allowing the reflected light, picked by the image pickup element, to be generated as an image for display on a monitor.

6 Claims, 16 Drawing Sheets

(52) U.S. Cl.
CPC   *A61B 2019/5408* (2013.01); *A61B 2019/5433* (2013.01); *A61B 2019/5441* (2013.01); *A61B 2019/5445* (2013.01); *A61B 2019/545* (2013.01)

(56) References Cited

U.S. PATENT DOCUMENTS

| | | | |
|---|---|---|---|
| 5,577,991 A | | 11/1996 | Akui et al. |
| 5,782,771 A | * | 7/1998 | Hussman ................. 600/478 |
| 5,853,366 A | * | 12/1998 | Dowlatshahi ............ 600/434 |
| 5,879,306 A | * | 3/1999 | Fontenot et al. ........... 600/473 |
| 6,181,960 B1 | * | 1/2001 | Jensen et al. ............. 600/431 |
| 6,293,911 B1 | * | 9/2001 | Imaizumi et al. .......... 600/160 |
| 6,336,904 B1 | * | 1/2002 | Nikolchev ................. 600/562 |
| 6,424,857 B1 | | 7/2002 | Henrichs et al. |
| 6,589,998 B1 | | 7/2003 | Bianchi et al. |
| 6,766,186 B1 | * | 7/2004 | Hoyns et al. ............... 600/431 |
| 7,014,839 B2 | * | 3/2006 | Klaveness et al. ......... 424/9.6 |
| 7,273,451 B2 | * | 9/2007 | Sekine et al. ............. 600/104 |
| 7,953,473 B2 | * | 5/2011 | Kaji et al. ................. 600/473 |
| 2002/0107437 A1 | * | 8/2002 | Sirimanne et al. .......... 600/407 |
| 2002/0143357 A1 | * | 10/2002 | Krag ......................... 606/179 |
| 2003/0013937 A1 | | 1/2003 | Tsujita et al. |
| 2003/0060718 A1 | | 3/2003 | Alam et al. |
| 2003/0092985 A1 | * | 5/2003 | Cox et al. ................. 600/436 |
| 2003/0135091 A1 | * | 7/2003 | Nakazawa et al. ......... 600/113 |
| 2003/0180221 A1 | * | 9/2003 | Miwa et al. ................ 424/9.6 |
| 2003/0192557 A1 | * | 10/2003 | Krag et al. ................. 128/898 |
| 2003/0233101 A1 | * | 12/2003 | Lubock et al. .............. 606/116 |
| 2004/0138555 A1 | * | 7/2004 | Krag et al. ................. 600/424 |
| 2004/0162469 A1 | * | 8/2004 | Imran ........................ 600/310 |
| 2004/0193044 A1 | * | 9/2004 | Burbank et al. ............ 600/431 |
| 2004/0225191 A1 | * | 11/2004 | Sekine et al. ............. 600/178 |
| 2005/0049489 A1 | * | 3/2005 | Foerster et al. ............ 600/431 |
| 2005/0063908 A1 | * | 3/2005 | Burbank et al. ............ 424/9.5 |
| 2005/0080337 A1 | * | 4/2005 | Sirimanne et al. .......... 600/431 |
| 2005/0080338 A1 | * | 4/2005 | Sirimanne et al. .......... 600/431 |
| 2005/0165305 A1 | * | 7/2005 | Foerster et al. ............ 600/431 |
| 2005/0255045 A1 | * | 11/2005 | Woltering ................. 424/9.34 |
| 2006/0036158 A1 | * | 2/2006 | Field et al. ................. 600/414 |
| 2006/0036159 A1 | * | 2/2006 | Sirimanne et al. .......... 600/414 |
| 2006/0036165 A1 | * | 2/2006 | Burbank et al. ............ 600/431 |

OTHER PUBLICATIONS

Search Report issued by European Patent Office on Mar. 24, 2014 in connection with corresponding EP patent application No. 10 013 002.0.

* cited by examiner

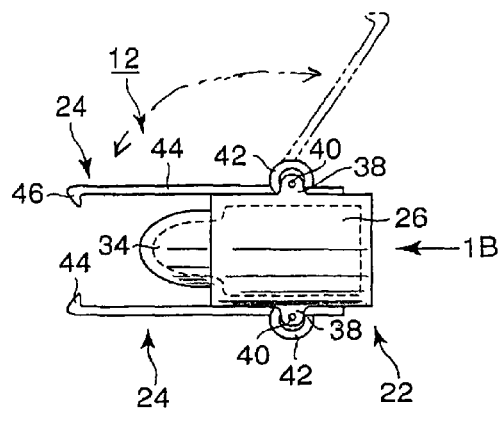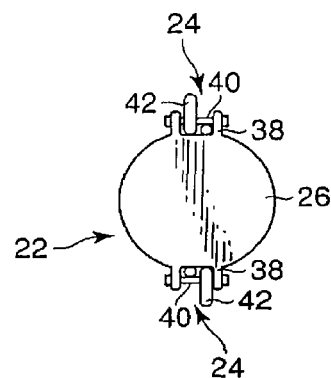
FIG.2A   FIG.2B
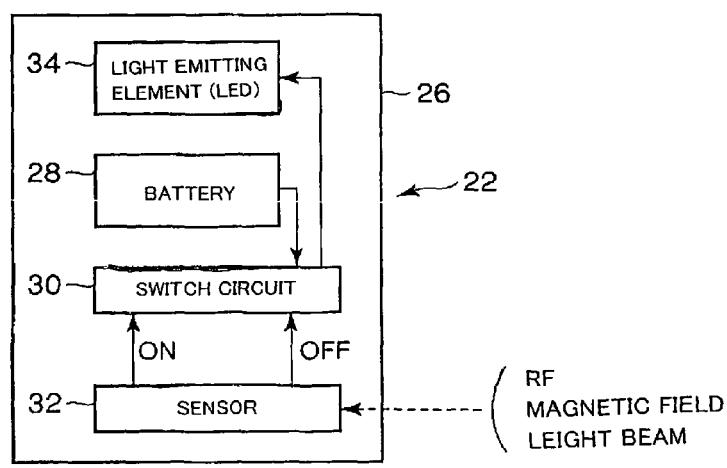
FIG.2C

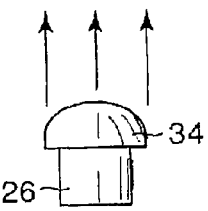
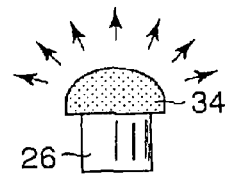
FIG.11A  FIG.11B
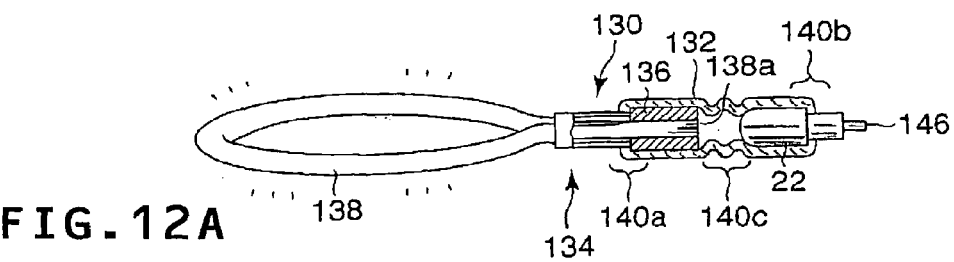
FIG.12A
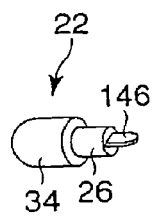
FIG.12B

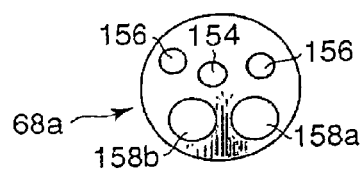
FIG.14A
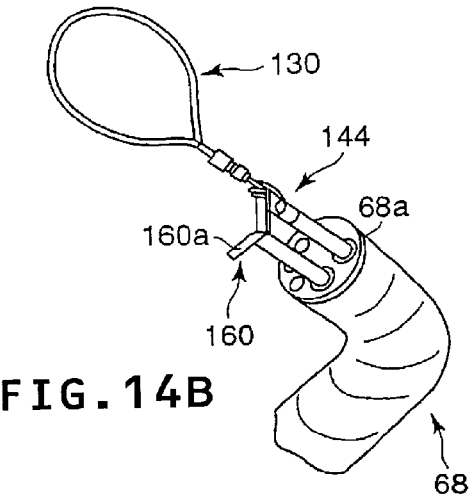
FIG.14B
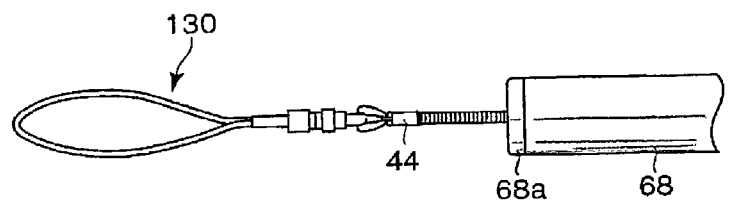
FIG.14C
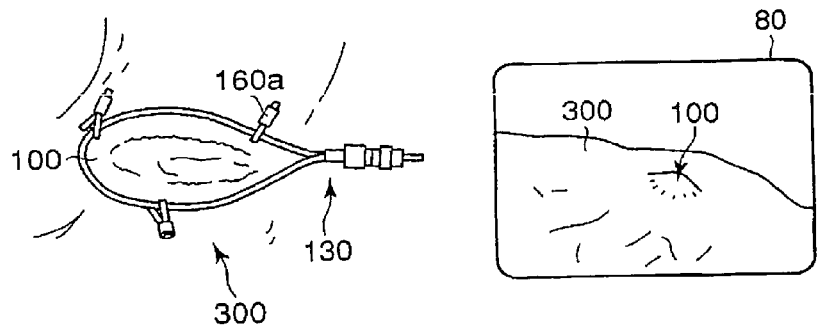
FIG.15A
FIG.15B

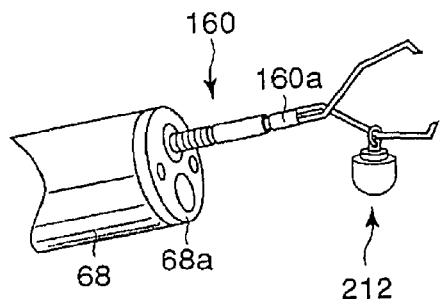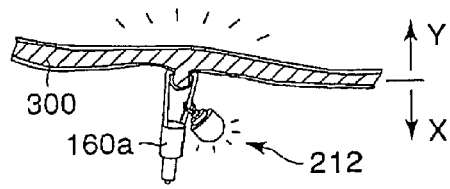
FIG. 18A  FIG. 18B
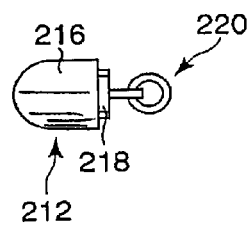
FIG. 19A
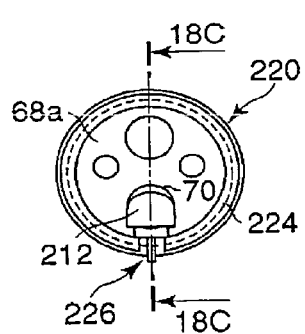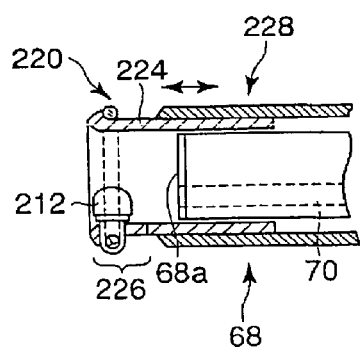
FIG. 19B  FIG. 19C

LIGHT MARKER FOR INDWELT USE IN PATIENT'S BODY AND FOR IDENTIFICATION OF LESIONS INSIDE PATIENTS TUBULAR ORGAN USING THE LIGHT MARKER

CROSS-REFERENCE TO RELATED APPLICATIONS

The present application is a continuation under 37 C.F.R. §1.53(b) of prior application Ser. No. 11/052,575 filed Feb. 7, 2005, entitled METHOD OF IDENTIFYING A LESION INSIDE PATIENT'S TUBULAR ORGAN, the entire contents of which are incorporated by reference herein, and further claims priority to and incorporates herein by reference Japanese Patent Application No. 2004-030509 filed on Feb. 6, 2004.

BACKGROUND OF THE INVENTION

1. Technical Field

The present invention relates to a lesion identification system for surgical operation for identifying a marker indicative of a location of a lesion of an organism.

2. Related Art

In modern surgical operations, various attempts have heretofore been undertaken to provide techniques known in the art to assist operations using a marker, placed prior to executing the operations and indicative of a location of a lesion in an internal site of a patient, as a field mark. As for these techniques, various techniques have been proposed in the related art.

For instance, Japanese Patent Publication No. 2794162 discloses an operation marker. The operation marker is comprised of a marker needle that has one end to which a lead wire is fixedly fastened. With such a structure, as the marker needle is indwelt in a lesion inside the patient prior to the execution of surgeries when executing, for instance, a lung surgery with the use of thoracoscope and a lever surgery with the use of a laparoscope, the marker needle is left with the lead wire exposed in the internal part. For this reason, the surgery can be executed using the lead wire as a marker.

However, since there is a probability for the surgery marker to be inserted to the lesion by penetrating through a normal site on a transcutaneous fashion, lesion cells scatter, resulting in dissemination to occur.

Further, Japanese Patent Provisional Publication No. 3-78 discloses a tube with a magnet for an organism. The tube, adapted for insertion to the organism, has a distal end to which a magnet is fastened, and magnetic fluxes resulting from the magnet are detected at an outside of the organism. Then, it becomes possible to detect a location of the distal end of the tube indwelt in the organism for non-invading ability.

However, when executing endoscopic treatment to the organism, the tube with the magnet for the organism is hard to take a proper response to an observation image of an endoscope even if the location of the magnet is detected.

When treating the lesion inside a digestive tract such as, for instance, a stomach, a rigidscope is probable to be used to execute an endoscopic treatment. One example of a technique for treating the lesion in such a case is described below. A soft endoscope is introduced to an inside of a stomach through a mouth and, for instance, a light is dimmed. When this takes place, using an illumination light from a light source of the endoscope allows a location of a lesion to be confirmed. Then, a laparoscope is inserted to a position suitable of the patient for treating an identified lesion, upon which the lesion is treated.

However, in such a case, a need arises for a flexiblescope, unnecessary for surgical operation per se, to be prepared only for the confirmation of the location of the lesion (operation site) and, in addition, it is required to keep an operator who has an ability to manipulate the flexiblescope. Furthermore, after the operations have been completed, there is a need for rinsing, disinfecting and clearing off the endoscope used for confirming the location of the operation site. For this reason, using the endoscope just for the positional confirmation to be executed during surgical treatment is disadvantageous because of an increase in labor hours, such as preparation and clearing off of the instrument, cumbersome and complicated techniques, keeping of the operator and increased costs.

As proposals for further improving the technique of utilizing the illumination light of the endoscope, a luminous marking clip has been known from Japanese Utility Model Registration Publication No. 3027808. The marking clip incorporates a light emitter and is attached to an inner wall of an organ such as a digestive tract. This allows an operator to look at a gleaming clip at an outside of the organ for the confirmation of a location of a lesion. However, this clip is used for visual observation and it is sometime hard to view the light emitted from the clip, providing a difficulty in usage. This light gleams to the extent as if the illumination of the endoscope is substituted to the light emitter associated with the clip.

Another technique has been known. That is, when executing treatment on a lesion inside, for instance, a large intestine on a laparoscopic fashion, a clip is preliminarily fixed to a surrounding of the lesion using a flexiblescope. When treating the lesion using a rigidscope, for instance, an X-ray is irradiated to the large intestine using an X-ray fluoroscope to obtain an X-ray transparent image. Thus, a location of the clip around the lesion is confirmed and, then, the lesion is surgically treated and extirpated.

However, in such a case, since the X-ray fluoroscope is used for confirming the location of the lesion, issues arise for the patient to be exposed to radioactivity. Also, the X-ray transparent image is completely different from the observation image obtained by the laparoscope, resulting in a difficulty in identifying the location of the lesion in relationship between the X-ray transparent image and the observation image from the laparoscope and confirming the relevant location concurrent with the treatment.

Furthermore, like the technology using the clip set forth above, in cases where the treatment is executed on the lesion inside the large intestine on a laparoscopic fashion, an ultrasonic device is used to apply an ultrasonic wave to a lesion for obtaining an ultrasonic image in the vicinity of the lesion under the use of a laparoscope. That is, the lesion is treated upon confirming the location of the clip around the lesion through the use of the ultrasonic image.

However, even in such a case, the ultrasonic image is completely different from the observation image from the laparoscope and it is hard to identify the location of the lesion in relationship between the ultrasonic image and the observation image of the endoscope.

In addition, like the two technologies using the clip set forth above, in cases where the treatment is executed on the lesion inside the large intestine on a laparoscopic fashion, tattooing pigment is preliminarily injected to a surrounding of the lesion using the flexiblescope in place of the clip described above. Then, since the pigment seeps to a serosa of a large intestine, the location of the lesion is confirmed using the laparoscope for treatment on the identified lesion.

However, with such a technique, if a tattooing process needs to be contrived as described below depending on a site or if a certain amount of time has elapsed after the application of tattooing pigment, probabilities take place with the scattering of tattooing pigment and the resultant difficulty in discriminating the lesion.

Additionally, another inconvenience takes place in the presence of attempts made to confirm the location of the lesion based on the technique of using the ultrasonic image set forth above or the technique of injecting tattooing pigment. For example, there is a probability wherein a lesion is present in a region on a dorsal side opposite to a region in which using a rigidscope allows an abdominal cavity to be observed. Under such a situation, since the technique of using the ultrasonic image undergoes a difficulty in transmitting an ultrasonic wave through the lesion in the presence of an air layer in an internal part of a tube of the large intestine, it becomes hard to obtain the ultrasonic image for identifying the lesion. Moreover, with the technique of injecting tattooing pigment, even when tattooing pigment is injected to the surrounding of the lesion, no tattooing pigment seep to a wall portion of the large intestine at an site in opposition to the lesion, resulting in a difficulty of identifying the lesion using the rigidscope.

SUMMARY OF THE INVENTION

The present invention has an object to identify a location of a lesion in an easy and reliable manner during surgical operations.

To this end, a lesion identification system for surgical operation of the present invention comprises a light marker adapted to be indwelt in the vicinity of a lesion inside an organ of an organism to be targeted, and a location-identifying device detecting a light, emitted from the light marker, at an outside of the organ to identify a location of the lesion.

With such a structure, the light marker is indwelt in the vicinity of the lesion, enabling the observation of the light (lights, such as a visible light and fluorescent light), emitted from the light marker, with the location-identifying device (for instance, an endoscope) via a wall portion of the organ. This enables the lesion inside the organ to be identified at the outside of the organ where the lesion is present.

Further, according to the present invention, a light marker for use in surgical operation is provided. In particular, the present invention provides the light marker adapted to be indwelt in the vicinity of a lesion inside an organ of an organism to be targeted, upon which a light emitted from the light marker is picked up at an outside of the organ for identifying the location of the lesion based on a location of the light on the pickup image. The light marker is comprised of en engagement member that allows the light emitter to be engageable with a wall of the organ, and an electric power supply supplying electric energy to the light emitter to allow the light emitter to emit a light after the engagement member is attached to the wall of the organ.

Further, according to another aspect of the light marker of the present invention, a light marker is provided that includes a light emitter using fluorescent substance that emits the light, and an engagement member operative to allow the light emitter to engage the wall of the organ. Furthermore, according to another aspect, the light marker includes liquid, composed of viscous substance mixed with fluorescent substance, which is adapted to be injected to a site underneath a mucous membrane of the lesion. In addition, according to a further aspect, the light marker includes a plurality of beady fluorescent balls, in each of which fluorescent substance is sealed, which is adapted to be introduced to the site underneath the mucous membrane of the lesion.

In the meanwhile, according to the present invention, a method of identifying a lesion for surgical operation is provided that includes indwelling a light marker in the vicinity of the lesion inside an organ of an organism to be targeted, picking up a light, emitted from the light marker, as an image at an outside of the organ, and identifying a location of the lesion based on a position of the light on the pickup image.

BRIEF DESCRIPTION OF THE DRAWINGS

In the accompanying drawings:

FIG. 2A is a schematic side view of the light source clip of a lesion identification system for surgical operation of a first embodiment according to the present invention;

FIG. 2B is a schematic view showing a status in which the light source clip is viewed in a direction as shown by an arrow 1B in FIG. 2A;

FIG. 2C is a schematic block diagram illustrating an internal structure of a receiver case shown in FIG. 2A;

FIG. 11A is a schematic view illustrating a light source that is configured such that the light source clip of the second embodiment emits a light straight ahead;

FIG. 11B is a schematic view of a light source configured such that the light source emits a light in a diffused fashion;

FIG. 12A is a schematic partially cut-away cross-sectional view showing a loop-shaped light marker for use in a lesion identification system for surgical operation of a third embodiment according to the present invention;

FIG. 12B is a schematic perspective view of a light source of the loop-shaped light marker;

FIG. 14A is a schematic view showing a distal end of an inserter section of an endoscope having two treatment implement insertion channels for use in the lesion identification system for surgical operation of the third embodiment;

FIG. 14B is a schematic view showing a status wherein a holder portion of the loop-shaped light marker is gripped in one treatment implement insertion channel by a holder forceps while a clip device is located on the other treatment implement insertion channel;

FIG. 14C is a schematic side view of an inserter section of an endoscope showing a status wherein the holder portion of the loop-shaped light marker is gripped in the treatment implement insertion channel by the holder forceps;

FIG. 15A is a schematic view illustrating a status wherein the loop-shaped light marker of the third embodiment is indwelt in an organism using clips;

FIG. 15B is a monitor screen of a rigidscope showing a status wherein a wall portion is pinched by the clips and observed at a side opposite to the loop-shaped light marker using a rigidscope;

FIG. 18A is a schematic perspective view illustrating a status in which a fluorescent light marker is entangled to an endoscope clip of the fourth embodiment;

FIG. 18B is a schematic view showing a status in which the clip is caused to engage a mucous membrane of an organism together with the fluorescent marker;

FIG. 19A is a schematic side view of a fluorescent marker for use in a lesion identification system for surgical operation of a fifth embodiment according to the present invention;

FIG. 19B is a schematic front view illustrating a status wherein the fluorescent marker is disposed in a distal end of an inserter section of an endoscope with a ring elastically deformed so as to allow the fluorescent marker to be mounted to an endoscope hood;

FIG. 19C is a partially cut-away cross-sectional view taken along a line 18C-18C of FIG. 19B;

DETAILED DESCRIPTION OF THE PREFERRED EMBODIMENTS

Now, best modes (hereinafter referred to as various embodiments) for carrying out the present invention are described with reference to the accompanying drawings.

First Embodiment

First, a first embodiment is described with reference to FIGS. 1 to 9A, 9B, 9C and 9D.

Figure 1:
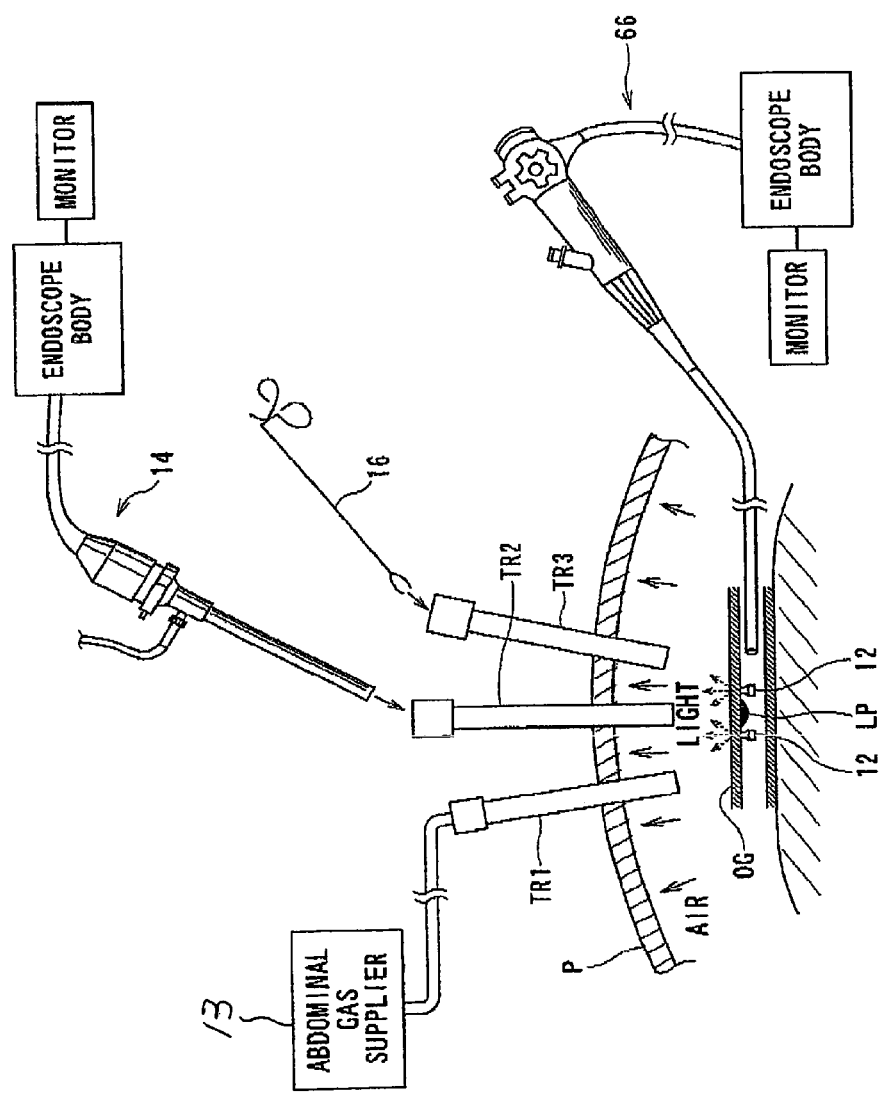
FIG. 1 is a typical view illustrating an overall schematic structure commonly used for the lesion identification systems for surgical operation of various embodiments according to the present invention.

As shown in FIG. 1, a lesion identification system for surgical operation of the presently filed embodiment is comprised of light source clips 12 (see FIG. 2A) each serving as a light marker (marker) having a light emitting function and a clipping function, an endoscope (first endoscope device) 66 (see FIG. 7A) serving as a soft scope for use in indwelling the light source clips 12, which will be described later, in the vicinity of a lesion, and an endoscope (second endoscope device) 14 (see FIG. 3A), serving as a rigidscope for surgical operation, which detect lights emitted by the light source clips 12.

In FIG. 1, further, reference P designates a patient (organ); OG designates an organ of the patient P to be targeted; and LP designates a lesion of the organ OG. Also, trocars TR1 to TR3 are inserted to a site of the patient P to be treated during operations. Among these trocars TR1 to TR3, for instance, the trocar TR1 is connected to an abdominal gas supplier 13 and a scope (inserter section) of the endoscope device 14 is inserted to an internal site while an instrument 16 is inserted to the internal site using the remaining trocar TR3.

As shown in FIGS. 2A and 2B, the light source clip 12 includes a light emitting light source 22, and a pair of engagement members (clip segments) 24 with which the light source 12 is caused to engage and fixed onto an organism.

The light source section 12 is comprised of a power supply means, a light emitting means that emits a light in response to electric power delivered from the power supply means, and a receiver case 26, formed in a cylindrical shape with a bottom wall, in which both the electric power supply means and the light emitting means are accommodated. As shown in FIG. 2C, the electric power supply means is comprised of a battery 28, a switch circuit 30 and a sensor 32, all of which is accommodated in the receiver case 26. The light emitting means includes an LED 34 that is electrically connected to the switch circuit 30. The LED 34 is mounted to the receiver case 26 so as to protrude forward from the receiver case 26. The sensor 32 is configured to detect radio waves, variation in a magnetic field or a light to deliver a resulting signal to the switch circuit 30. The switch circuit is supplied with electric power from the battery 28 in response to the signal from the sensor 32 to selectively supply electric power to the LED 34.

The engagement members 24 of the light source clip 12 serves as a fixing means by which the light emitting means, described later, is indwelt in and fixed to the internal site. The engagement members 24 are mounted to the receiver case 26. Formed on an outer periphery of the receiver case 26 is a pair of protrusions 38 formed with apertures, respectively. Pins 40 are inserted to the apertures of the protrusions 38, respectively. The pins 40 carry springs 42, respectively. The springs 42 are integrally formed with arms 44, each made of ultra-resilient alloy material, respectively. For this reason, the arms 44 are urged in given directions, respectively. In this case, the arms 44 are oriented in the same direction as the LED 34. The arms 44 have distal ends formed with claw portions 46, respectively. The claw portions 46 are placed in face-to-face relationship. The engagement members 24, formed in such configurations, are rotatable about axes of the pins 40 at angles of 180 degrees, respectively.

Figure 3A:
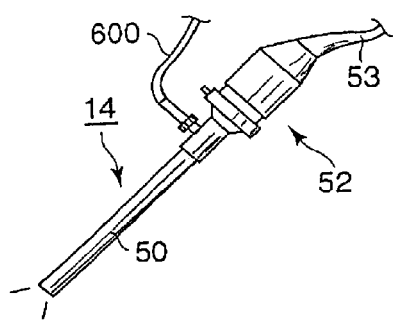
FIG. 3A is a schematic view of a rigidscope of the lesion identification system for surgical operation of the first embodiment.
Figure 3B:
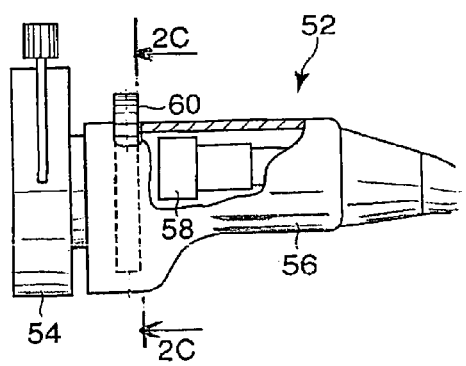
FIG. 3B is a schematic partly cut-away cross-sectional view of a camera head of the rigidscope.
Figure 3C:
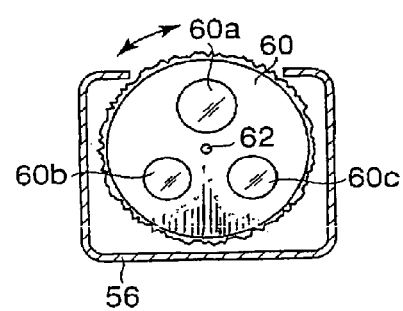
FIG. 3C is a schematic view of an adjustable filter section under a status taken on line 2C-2C of FIG. 3B.
Figure 4:
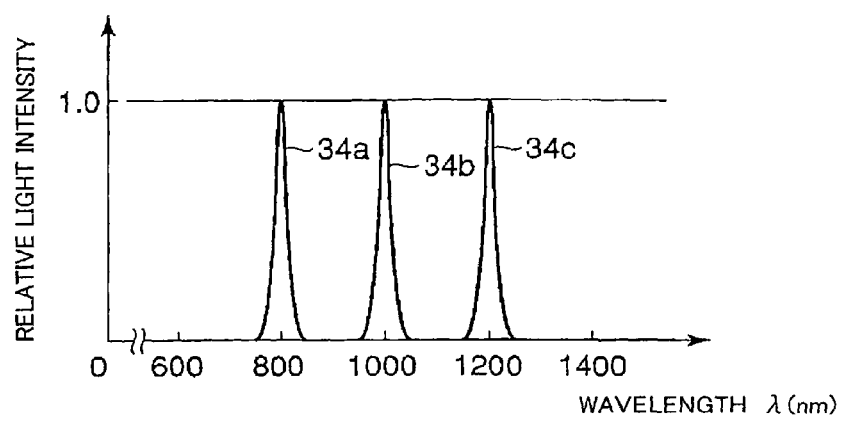
FIG. 4 is a graph showing a relative light intensity, of each of LEDs with wavelengths different from each other, in terms of a wavelength in the lesion identification system for surgical operation of the first embodiment.

The LEDs 34 of the light sources 22 have characteristics, depending on kinds, as exemplarily shown in FIG. 4 in an overlapped condition. In FIG. 4, the coordinate indicates relative light intensity and the abscissa indicates a wavelength λ (nm). In cases where a plurality of light source clips 12 is employed, there is a probability for the LEDs 34 of different kinds to be used with the characteristics shown in FIG. 3. Here, description is made of first to third LEDs 34a, 34b, 34c whose characteristics are different from each other.

As shown in FIG. 4, the first LED 34a emits a light with a peak value at a wavelength of 800 nm. The second LED 34b emits a light with a peak value at a wavelength of 1000 nm. The third LED 34c emits a light with a peak value at a wavelength of 1200 nm. The first to third LEDs 34a, 34b, 34c, with such characteristics, are mounted to the respective receiver cases 26 on opening sides thereof, by which the first to third light source clips 12a, 12b, 12c are respectively formed.

As for the endoscope 14 set forth above, a hard one is used which is introduced to an abdominal cavity from an outside of a body through, for instance, the trocar TR2 or the like. Therefore, as used herein, the "endoscope 14" is referred to as a rigidscope (optical viewing tube). As shown in FIG. 3A, the rigidscope 14 is comprised of an elongated hard inserter section 50, and a camera head 52 detachably mounted to a base of the inserter section 50. Disposed in the inserter section 50 are an illuminating and optical system (not shown) and an objective optical system (not shown) through which an illuminated site is observed. The objective optical system includes a relay lens through which an optical image, incident on the objective lens (not shown), is relayed to the base of the inserter section 50. The illuminating and optical system includes a light guide (not shown) through which an illumination light is guided from the camera head 52 to an illumination lens (not shown) at a distal end of the inserter section 50. Connected to the base of the inserter section 50 of the rigidscope 14 are a light guide cable 600 through which a light is guided to the illuminating and optical system, and the camera head 52 equipped with a universal cable 53 that transmits a pickup image from a CCD camera that will be described later.

As shown in FIG. 3B, the cameral head 52 includes a connector joint 54 connected to the base of the inserter section 50, and an optical element receiver 56. The optical element receiver 56 is comprised of a CCD element 58 that picks up an optical image relayed through the relay lens, and an adjustable filter section 60.

The CCD element 58 has a characteristic capable of picking up an optical image not only in a visible range (with a wavelength ranging from 380 nm to 780 nm) but also in a near-infrared range (with a wavelength ranging from 780 nm to 1300 nm). As shown in FIG. 3C, the adjustable filter section 60 is rotatable about an axis of a pivot shaft 62 and has first to third optical filters 60a, 60b, 60c with characteristics different from each other. With such arrangement, rotating the first to third optical filters 60a, 60b, 60c about the axis of the pivot shaft 62 of the adjustable filter section 60 for selection allows optical images with different wavelengths to be incident on the CCD element 58.

Figure 6A:
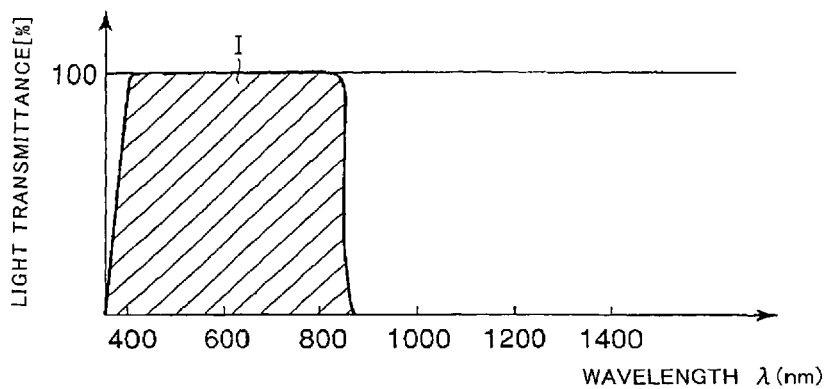
FIGS. 6A to 6C are graphs illustrating characteristics of optical filters located in the adjustable filter section of the lesion identification system for surgical operation of the first embodiment.
Figure 6B:
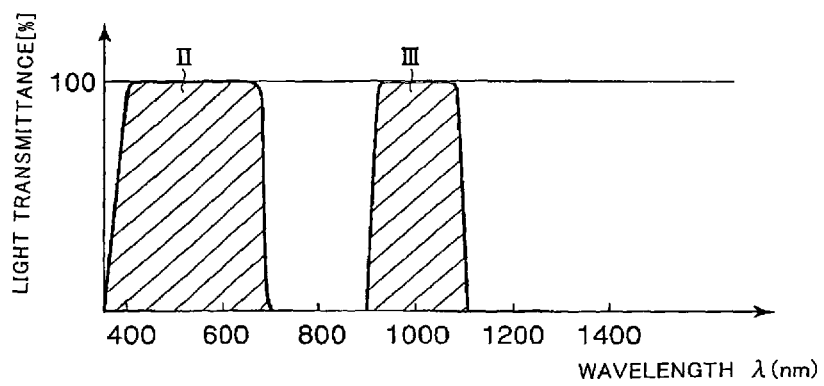
Figure 6C:
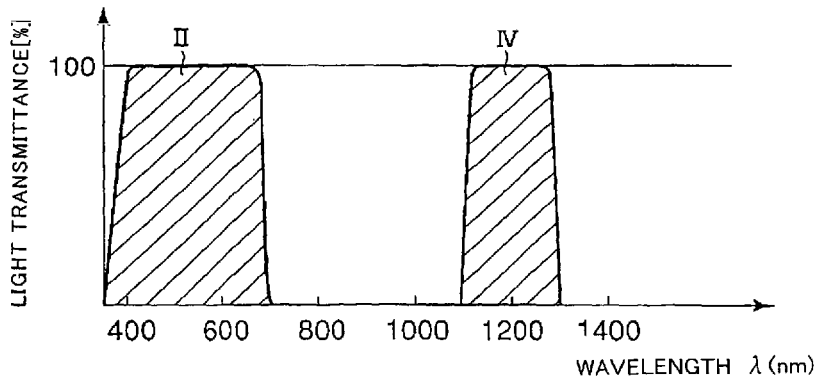

FIG. 6A shows a characteristic of the first optical filter 60a. FIG. 6B shows a characteristic of the second optical filter 60b. FIG. 6C shows a characteristic of the third optical filter 60c. In FIGS. 6A to 6C, the coordinates indicate light transmittances (%), respectively, and the abscissas indicate wavelengths λ (nm), respectively. Also, although all the light transmittances in FIGS. 6A to 6C are plotted in the order of 100%, it will be appreciated that, in actual practice, the light transmittance may be properly varied in use to values in the order of, for instance, 90% or 80%.

As shown in FIG. 6A, the first optical filter 60a has the characteristic (region I) that transmits a light with a wavelength ranging from, for instance, 380 nm to 850 nm. This covers the light in a nearly visible range. Additionally, this permits a light with a wavelength, partly involved in the visible range in a near-infrared range, to transmit through the first optical filter 60a.

As shown in FIG. 6B, the second optical filter 60b has a first characteristic (region II) that transmits a light with a wavelength ranging from, for instance, 380 nm to 780 nm and a second characteristic (region III) that transmits a light with a wavelength ranging from, for instance, 900 nm to 1100 nm. This covers the light in the nearly visible range. Additionally, this permits the light with the wavelength partly involved in the visible range in the near-infrared range. Also, the light transmittances in the regions II, III may differ from each other or may be varied to suitable values depending on a detection status (caused by a wall thickness of a site to be treated or a light transmittance) of a light with a wavelength in an infrared range.

As shown in FIG. 6C, the third optical filter 60c has the same characteristic (region II) as that of the region II of the second optical filter 60b and has another characteristic (region IV) that transmits a light with a wavelength ranging from, for instance, 1100 nm to 1300 nm. This covers the light in the nearly visible range. Additionally, this permits the transmission of a light with a wavelength partly (on a side closer to an infrared range with respect to the visible range) involved in the near-infrared range. Also, the light transmittances in the regions II, IV may differ from each other or may be varied to suitable values depending on a detection status of the light with the wavelength in the infrared range.

Therefore, properly selecting the first to third optical filters 60a, 60b, 60c enables the CCD element 58 to pick up observation images in the visible range and the near-infrared range, respectively. Although the observation image (light) in the near-infrared range is not present in the visible range and invisible in normal practice, connecting an image processor (recognition means) (not shown) to the CCD element 58 provides a capability of executing image processing to allow the image to be viewable (visible). The image processor has a function to make it possible for a light with a wavelength in a near-infrared range to be visible while having a function to modulate a contrast of the image and make contour-emphasis. Then, an image (detected light) in the near-infrared range is superimposed on an observation image in the visible range for display over a monitor (not shown) to which the image processor is connected.

Figure 7A:
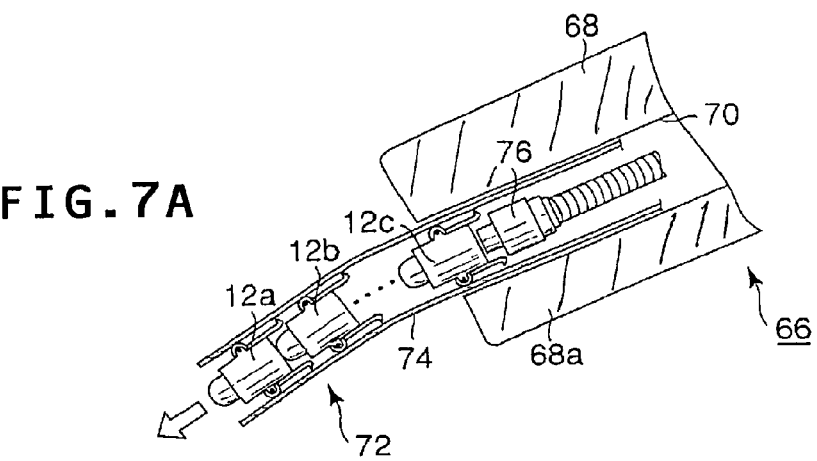
FIG. 7A is a schematic cross sectional view of a flexiblescope to be used when the light source clip of the first embodiment is indwelt.

As shown in FIG. 7A, the lesion identification system for surgical operation further includes the flexiblescope (first endoscope) 66 that is adapted for insertion to an internal part of an organ through a nose, a mouth or an anus to allow the light source clips 12 to be indwelt to a site close proximity to the lesion or to treat the same. That is, the endoscope 66 is comprised of an elongated inserter section 68 and a manipulator section (not shown) mounted to a base of the inserter section 68. The inserter section 68 includes a flexible tube (not shown), which is flexible and connected to the manipulator section, and a flexing segment (not shown) disposed on a distal end of the flexible tube. The manipulator section is able to allow the flexing segment of the inserter section 68 to be operated in a flexing ability.

Disposed in the inserter section 68 of the endoscope 66 are an illumination optical system (not shown) for illuminating an object to be treated, an objective optical system (not shown) through which an illuminated site is observed, and a treatment implement insertion channel (forceps channel) 70. The treatment implement insertion channel 70 is available to insert a clip applicator 72 through which the light source clips 12 are guided to a site close proximity to, for instance, a lesion.

The clip applicator 72 is comprised of a tabular member 74 in which the plural light source clips 12 are internally arrayed under a cascaded condition, and a pusher 66 by which the light source clip 12, placed in the rearmost side closer to the base of the tubular member 74, is pressed. As shown in a phantom line in FIG. 2A, the engagement members 24 of the respective light source clips 12 are disposed such that the claws 46 are oriented rearward against forces of the springs 42. When this takes place, the light source clips 12 are set out such that the LED 34 is closer to a distal end of the tubular member 74. For this reason, as the pusher 76 is moved forward in the tubular member 74, the light source clips 12 are sequentially released from the distal end of the tubular member 74 to enable the engagement members 24 of each light source clip 12 to clamp a mucous membrane of the organism due to urging forces of the springs 42. When this takes place, the light source clips 12 are preferably filled inside the tubular member 74 to allow the first to third light source clips 12a, 12b, 12c, which have the first to third LEDs 34a, 34b, 34c with different characteristics, respectively, to be sequentially released.

Figure 7B:
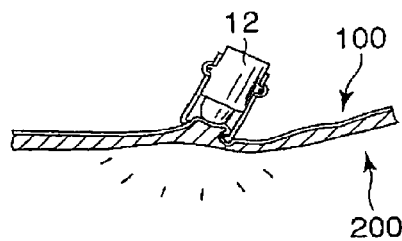
FIG. 7B is a schematic view illustrating a status in which an LED is caused to emit a light with the light source clip engaging a mucous membrane of an organ.
Figure 8:
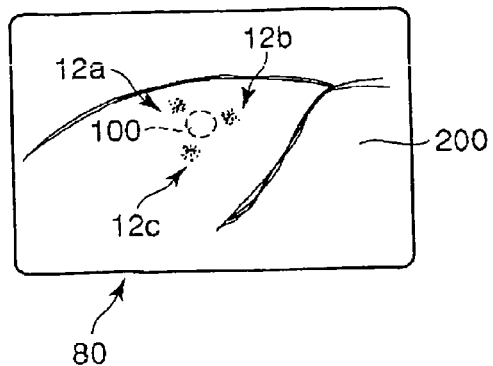
FIG. 8 is a monitor screen of a rigidscope in which an emitted light, resulting when the light source clip, indwelt in side a lung, is caused to emit the light, is displayed in a superimposed fashion with an observation image obtained when an exterior of the lung is observed.

Now, reference is made to FIGS. 7 to 9 to describe a basic sequence of operations for identifying the lesion 100 such as, for instance, a lung 200 or a large intestine 300, with the rigidscope 14 through the use of the lesion identification system for surgical operation of the presently filed embodiment. First, description is made of a case in which the lesion 100 is present in the lung 200 with reference to FIGS. 7 and 8.

The inserter section 68 of the endoscope 66 is inserted to an internal part of the lung 200 through a bronchus until a distal end 68a of the inserter section 68 is introduced to a site close proximity to the lesion 100. As shown in FIG. 7A, the clip applicator 72, whose treatment implement insertion channel 70 accommodates therein the plural light source clips 12 arranged in the cascaded manner, is inserted. Subsequently, the distal end of the tubular member 74 of the clip applicator 72 is caused to protrude relative to the distal end 68a of the inserter section 68 of the endoscope 66 until the distal end of the tubular member 74 is brought into a pressured contact with the site to be clamped under which the pusher 76 is moved. Then, as shown in FIG. 7B, the first light source clip 12a is released to clamp the mucous membrane at the site close proximity to the lesion 100 of a wall portion inside the lung 200.

When this takes place, the first light source clip 12a, released from the clip applicator 72, permits the arms 44 to rotate at the angle of 180 degrees about the axes of the respective pins 40 due to the urging forces of the associated springs 42 for thereby causing the claws 46 to clamp the mucous membrane. Thereafter, the second and third light source clips 12b, 12c are similarly released from the distal end of the tubular member 74 to allow these clips to engage the mucous membrane of the lung 200 (see FIG. 7B) in a way to surround the lesion 100. That is, as shown in FIG. 8, the first to third light source clips 12a, 12b, 12c are fixed to the mucous membrane so as to surround the lesion 100.

Subsequently, an initiation signal, such as for instance a radio wave, which exceeds a given threshold value, is applied to the sensors 32 of the first to third light source clips 12a, 12b, 12c, upon which the switch circuits 30 are rendered operative to allow the battery 28 to supply electric power to the first to third LEDs 34a, 34b, 34c. When this happens, the first to third LEDs 34a, 34b, 34c of the first to third light source clips 12a, 12b, 12c, respectively, operate to emit lights. Under such a condition, after confirming operating conditions of the first to third light source clips 12a, 12b, 12c with the rigidscope 14, the inserter section 68 of the endoscope 66 is taken out of the internal part of the lung 200.

Figure 5:
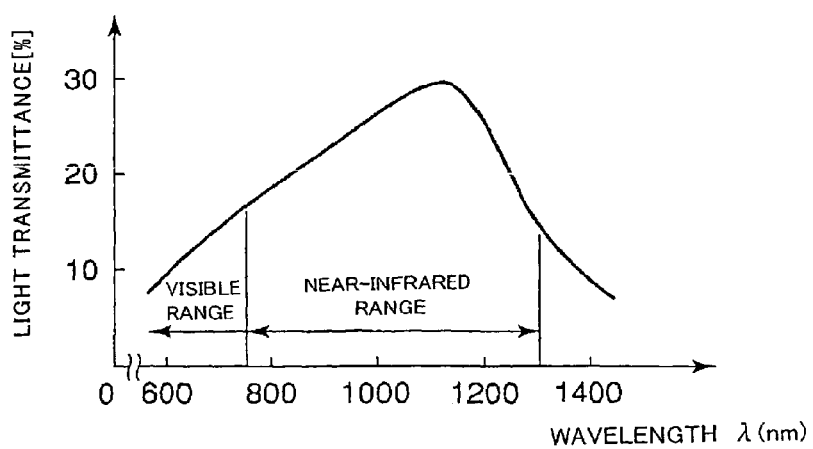
FIG. 5 is a graph showing a light transmittance relative to an organism.

By the way, the coordinate in FIG. 5 represents a light transmittance with respect to an organism and the abscissa represents a wavelength $\lambda$ (nm). As shown in FIG. 5, a light of a wavelength in a near-infrared range has a higher transmittance with respect to the organism than that of a light of a wavelength in the visible range. Suppose that the first optical filter 60a is selected by the adjustable filter section 60 of the camera head 52 of the rigidscope 14. A light (with a wavelength of 800 nm) emitted from the first LED 34a of the first light source clip 12a transmits through the wall portion of the lung 200 and is picked up by the CCD element 58 of the rigidscope 14 (see FIG. 6A). As shown in FIG. 8, the lights emitted from the first to third light source clips 12a, 12b, 12c are made visible (visualization) upon image processing and displayed together with an optical image from the rigidscope 14 in the visible range over the monitor (recognition means) 80 via the image processor. The optical image in the visible range forms an opposite real image with respect to a side in which the light source clips 12 are indwelt at the wall portion of the lung 200.

Suppose that the second optical filter 60b is selected with the adjustable filter section 60 of the rigidscope 14. A light (with a wavelength of 1000 nm) emitted from the second LED 34b of the second light source clip 12b transmits through the wall portion of the lung 200 and picked up by the CCD element 58 of the rigidscope 14. The pickup image and the optical image, in the visible range, of the rigidscope 14 are displayed over the monitor 80 shown in FIG. 8 (see FIG. 6B).

Suppose that the third optical filter 60c is selected with the adjustable filter section 60 of the rigidscope 14. A light (with a wavelength of 1200 nm) emitted from the third LED 34c of the third light source clip 12c transmits through the wall portion of the lung 200 and picked up by the CCD element 58 of the rigidscope 14. The pickup image and the optical image, in the visible range, of the rigidscope 14, are displayed over the monitor 80 shown in FIG. 8 (see FIG. 6C).

That is, appropriately rotating the adjustable filter section 60 about the axis of the pivot shaft 62 for selecting the first to third optical filters 60a, 60b, 60c allows respective locations of the first to third light source clips 12a, 12b, 12c in the vicinity of the lesion 100 to be observed using the rigidscope 14. For this reason, the positional relationship among the first to third light source clips 12a, 12b, 12c can be identified. Since the lesion 100 remains inside the first to third light source clips 12a, 12b, 12c, using the rigidscope 14 enables the location of the lesion 100 to be identified at an outside of the lung 200. Accordingly, the lesion 100 inside the lung 200 can be recognized (for identification) using the monitor 80 connected to the rigidscope 14 and can be observed with the observation image of the outside of the lung 200 in an overlapped condition.

Thereafter, under the observation through the rigidscope 14, the lesion 100 and the light source clips 12 are surgically incised in a lump. That is, the lesion 100 is collectively incised with the light source clips 12 attached to the lesion 100. When this takes place, since the lesion 100 is collectively incised, it becomes possible to easily recognize a configuration under which the lesion 100 is present in the organism even after the lesion 100 has been incised. Under such a status, the first to third LEDs 34a, 34b, 34c, with the characteristics different from each other, of the first to third light source clips 12a, 12b, 12c are operated to emit lights which in turns transmit through the lesion 100, permitting the lights to be picked up by the CCD element 58. Then, upon comparing the pickup image to the status wherein the lesion 100 was present in the organism, it is possible to easily specify a direction in which the lesion 100 was present in the organism. That is, confirming the extirpated lesion 100 in the presence of the light source clips 12 enables not only the configuration when the lesion 100 was present in the organism but also the direction in which the lesion 100 was present in the organism to be easily recognized. Thus, it becomes possible to confirm tissues upon excision and extirpation while understanding the site (direction) to be additionally incised at once even when a leftover lesion exists. Further, due to collective incision of the lesion 100 together with the light source clips 12, no harm is caused to the organism.

Also, though not shown, the adjustable filter section 60 may include an optical filter with a characteristic that transmits a light with wavelengths in a visible range and a near-infrared range. By so doing, an observation image in the visible range can be obtained, while making it possible to recognize the locations of the first to third light source clips 12a, 12b, 12c at the same time.

Figure 9A:
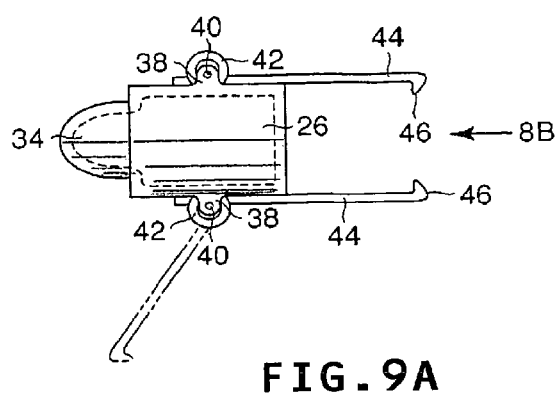
FIG. 9A is a schematic side view of the light source clip of the lesion identification system for surgical operation of the first embodiment.
Figure 9B:
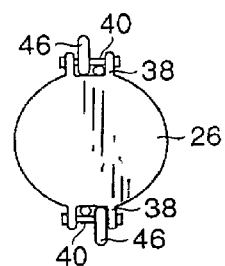
FIG. 9B is a schematic view showing a status in which the light source clip is observed in a direction as shown by an arrow 8B in FIG. 9A.
Figure 9C:
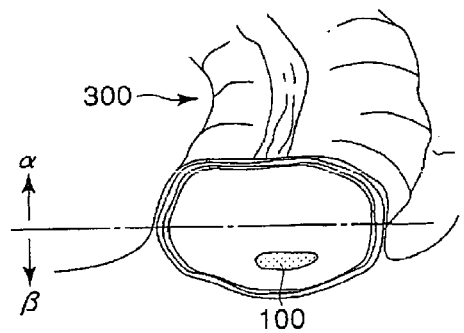
FIG. 9C is a cross-sectional view of a large intestine inside of which a lesion is present.

Further, the light source clip 12 may take the form of a structure shown in FIGS. 9A and 9B. As shown in FIG. 9A, the engagement members 24 of the light source clip 12 are formed in a direction opposite to that in which the engagement members 24 of the light source 12 are located in FIG. 2A. Under such a situation, the engagement members 24 are urged in a direction opposite to the LED 34 of the receiver case 26.

With such a structure, a plurality of light source clips 12 are set out in the distal end portion of the tubular member 74 of the clip applicator 72 such that the receiver case 26 is closer to the distal end of the tubular member 74 (not shown).

Next, description is made of operations when the lesion 100 is present in the large intestine 300 shown in FIG. 8C. For instance, suppose that the lesion 100 is not present in a region α in front of a body (on an abdominal cavity side) but present in a region β on a dorsal side.

Figure 9D:
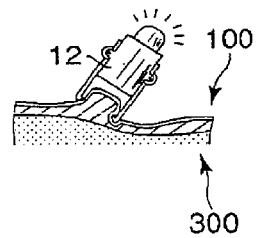
FIG. 9D is a schematic view illustrating a status in which the light source clip is indwelt in the vicinity of a lesion shown in FIG. 9C so as to illuminate a abdominal cavity of a large intestine.

The light source clip 12 is clamped to and indwelt on a mucous membrane in an internal part of the large intestine 300, as shown in FIG. 9D, using the clip applicator 72 disposed in the treatment implement insertion channel 70 of the endoscope 66 that is inserted through an anus. When the LED 34 of the light source clip 12 is turned on to emit a light, the light is illuminated on a wall portion on the region α in opposition to the lesion 100. The light, with a wavelength transmitted through an illuminated wall portion, is picked up by the CCD element 58 of the rigidscope 14. The light of the LED 34 is visualized on the monitor, thereby identifying the lesion 100. Therefore, not only in cases where the lesion 100 is present on a side close proximity to the distal end of the inserter section 50 of the rigidscope 14 in the large intestine 300, but also in cases where the lesion 100 is remote from the distal end of the inserter section 50 of the rigidscope 14, the light transmitting through the wall portion of the large intestine 300 is picked up to allow the light to be displayed together with a real image, enabling a location of the lesion 100 to be easily visually recognized at an outside of the large intestine 300. That is, the location of the lesion 100 can be easily identified using the rigidscope 14.

Also, while the presently filed embodiment has been described with reference to an exemplary implementation wherein the operations are executed using the plural light source clips 12 with the LEDs 34 of different kinds, an alternative may include a single light source clip 12 in use and another alternative may include light source clips 12 with LEDs 34 of the same kind.

As set forth above, with the lesion identification system for surgical operation of the presently filed embodiment, there are advantageous effects listed below.

Under a condition where the clip applicator 72 is inserted to the treatment implement insertion channel 70 of the endoscope 14 through which the distal end 68a of the inserter section 68 is introduced to the site close proximity to the lesion 100 of the organ, using the clip applicator 72 enables the light source clips 12 to be easily indwelt around the lesion 100 of the organ.

Due to an ability of the LED 34 of the light source clip 12 wherein the light, with the wavelength in the near-infrared range, which is easier to transmit through the wall portion of the organ than that with the wavelength in the visible range, is emitted in the internal part of the organ, the transmitted light can be picked up using the CCD element 58 of the rigidscope 14 at the outside of the organ.

For this reason, by image processing the light in the near-infrared range with the image processor to allow the light, subjected to image processing, to be displayed with the real image in the visible range in a superimposed manner, the location of the lesion 100 can be easily recognized at the outside of the organ on real time basis. That is, the location of the lesion 100 can be identified without difficulty. Also, the use of the endoscope provides an easier observation at part of the wavelengths of the near-infrared range, use of the wavelengths being desired for visual observation. This manner provides the ease of identifying the lesion.

Further, since the rigidscope 14 and the camera head 52, employed for surgical operation through the use of the endoscope, are configured to originally have such an image pickup function, no other devices are needed for identifying the lesion 100, making it possible to effectively utilize a space in an operation room. Thus, the lesion 100 can be identified with a structure that is low in costs.

By so doing, it becomes possible to provide a lesion identification system for surgical operation that is less expensive and simple in operation, wherein merely confirming an observation image of the rigidscope 14 enables the lesion 100 to be identified on real time basis.

Second Embodiment

Next, a second embodiment is described with reference to FIGS. 10A-10C and 11A-11B. This embodiment is a modified form of the first embodiment and the same component parts as those described in the first embodiment bear like reference numerals to omit detailed description. Hereunder, the way of such omission may similarly apply to third to ninth embodiments.

Figure 10A:
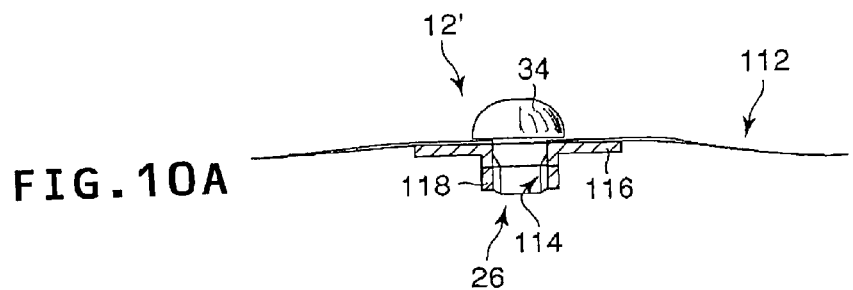
FIG. 10A is a schematic side view of a light source clip for use in a lesion identification system for surgical operation of a second embodiment according to the present invention.

As shown in FIG. 10A, a light marker 12' of a lesion identification system for surgical operation of the presently filed embodiment differs from the light source clip 12, serving as the light marker, of the first embodiment in shapes of the engagement members 24 and the receiver case 26. The receiver case 26 has the same internal structure as that of the first embodiment described above.

An LED 34 of the light marker 12' is formed in a hemispheric shape. A center of the LED 34 and a center of the receiver case 24 are aligned on the same axis and a diameter of the LED 34 is formed in a larger size than that of the receiver case 24.

Further, the engagement members 24 are configured in a structure as mentioned below. Disposed in a step between the LED 34 and the receiver case 26 is a mesh-like member 112. The receiver case 26 has an outer periphery formed with a threaded portion 114. The mesh-like member 112, disposed on an outer periphery of the receiver case 26, is screwed onto the threaded portion 114 by a nut 118 formed with a discoid flange portion 116.

Now, reference is made to FIG. 10 to describe operations of indwelling the light marker 12' with the mesh-like member 112 on the lesion 100 using the lesion identification system for surgical operation of the presently filed embodiment.

Figure 10B:
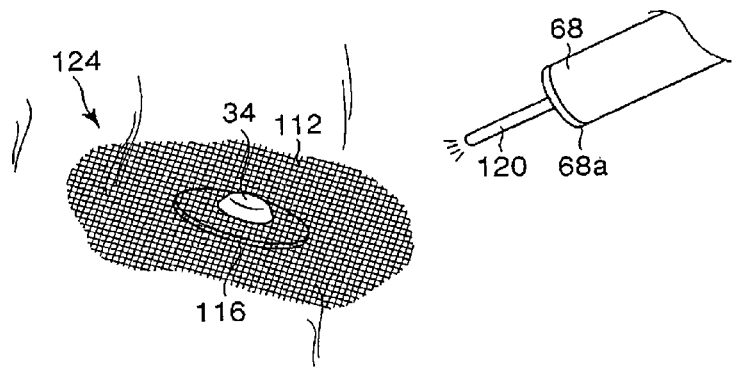
FIG. 10B is a schematic view illustrating a status in which the light source clip shown in FIG. 10A is placed over a lesion and adhesive is sprayed using an endoscope.
Figure 10C:
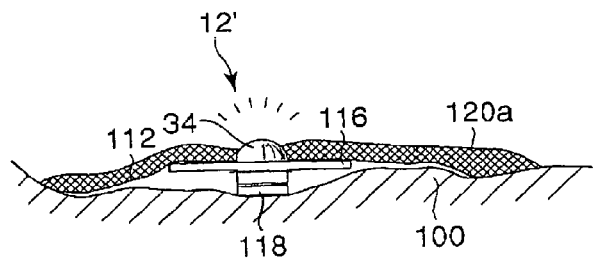
FIG. 10C is a schematic cross-sectional view showing a status in which the light source clip shown in FIG. 10B and the lesion are excised in an appropriate direction.

As shown in FIG. 10B, an organism-adapted adhesive spray catheter 120 is introduced from a distal end of the treatment implement insertion channel 70 of the endoscope 66 and organism-adapted adhesive 120a is sprayed onto the mesh-like member 112 of the light mark 12' located in the vicinity of a lesion 100 of a digestive tract wall 124. Then, the light marker 12' is adhered to a mucous membrane of an organism together with the mesh-like membrane 112. In this case, adhesive 120a may be sprayed onto an outer circumferential periphery of the mesh-like member 112 or an overall area of the mesh-like member 112.

Under such a situation, when the LED 34 of the light marker 12' is caused to emit a light, the presently filed embodiment provides the same effects as those described in connection with the case where the lesion 100 is present in the large intestine 300 shown in FIG. 8C related to the first embodiment.

Also, though not shown, under a situation where the LED 34 is brought into abutting contact with the digestive tract wall (lesion 100), it is possible to obtain the same effects as those described above with reference to the situation where the lesion 100 is present under the positional relationship between the light source clips 12 and the observing means (rigidscope 14) shown in FIGS. 7B and 8 related to the first embodiment. Although the first embodiment has been described with reference to the implementation where the light source clips 12 are indwelt in the vicinity of the lesion 100, the second embodiment enables the light marker 12' to be indwelt on an upper side of the lesion 100. Therefore, when observing the lesion 100 using the rigidscope 14, the position of the light from the LED 34 of the light marker 12' can be identified as the lesion 100.

Further, while the second embodiment has been described in conjunction with the use of the mesh-like member 112, the mesh-like member 112 may be replaced with a sheet-like member through which adhesive 120a permeates.

Also, with the presently filed embodiment, while a direction (light path) of the light emitted from the LED 34 is oriented in a radial direction of the hemispheric LED, the LED 34 may be configured to allow the light path to extend straight. That is, an alternative may include the LED 34 with linearity in a light path. Moreover, another alternative may take the form of a structure wherein an outer surface of the LED 34 is formed in a roughened state with an uneven surface to diffuse the light. The rate of diffusion and linearity of light emitted from the LED 34 may be appropriately set depending on the positional relationship between the lesion 100 and the rigidscope 14 and accuracy of detecting a lesion position.

Third Embodiment

Now, reference is made to FIGS. 12A-12B to 15A-15B to describe a third embodiment.

As shown in FIG. 12A, a loop-shaped light marker 130 is employed in place of the light markers (light source clips 12) described with reference to the first embodiment. The loop-shaped light marker 130 is comprised of a tubular holder 32, a light source 22 mounted inside the holder 132, and a light guide 134 through which a light emitted from the light source 22 is guided to an outside of the holder 132.

The light guide 134 is comprised of a tubular light guide base 136 that is retained by caulking a distal end of the holder 132, and a light guide 138 having both ends disposed in an inner aperture of the base 136 and mounted to the same to allow the light guide 138 to extend from the base 136 in a loop shape to serve as a loop-shaped light source. That is, the base 136 has a distal end that is fixedly secured to the holder 132 by means of a first caulked portion 140a.

The light source 22 is fixed in position on a base side of the holder 132 by means of a second caulked portion 140b. In particular, an outer periphery of the receiver case 26 of the light source 22 is fixedly secured to the holder 132 by means of the second caulked portion 140b.

Formed on the holder 132 at an intermediate position between the light source 22 and the light guide 134 is a third caulked portion 140c. Therefore, the third caulked portion 140c defines a distance between the both ends of the light source 22 and the light guide 138. It is so designed such that a light emitted from the LED 34 is condensed at an end portion 138a by means of such a restricted distance. As a consequence, a strong light is efficiently guided to the light guide 138 from the end portion 138a of the light guide 138 at all times. In order for a portion of the introduced light to leak from the light guide 138, the light guide 138 has one end face of a fiber is stripped to be bared.

The light source 22 is comprised of an electric power supply means, a light emitting means emitting a light upon receipt of electric power supply from the electric power supply means, and a receiver case 26, formed in a cylindrical shape formed with a bottom wall, which accommodates therein the electric power supply means and the light emitting means. Formed on the receiver case 26 at a position (the bottom wall) remotest from the LED 34 of the receiver case 26 to be integral with the receiver case 26 is, for instance, a flat plate-like retainer 140 that is adapted to be gripped by a forceps 144 (see FIG. 14B).

Figure 13A:
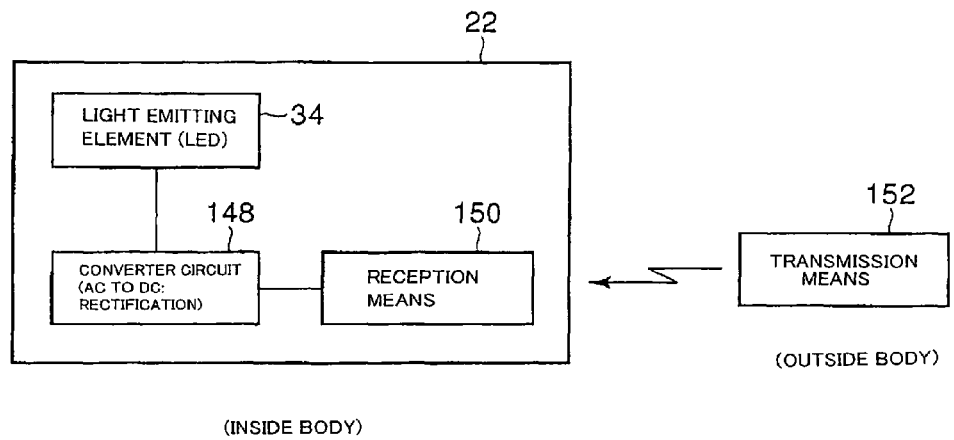
FIG. 13A is a schematic block diagram illustrating an internal structure of a receiver case of the light source of the loop-shaped light marker of the third embodiment.
Figure 13B:
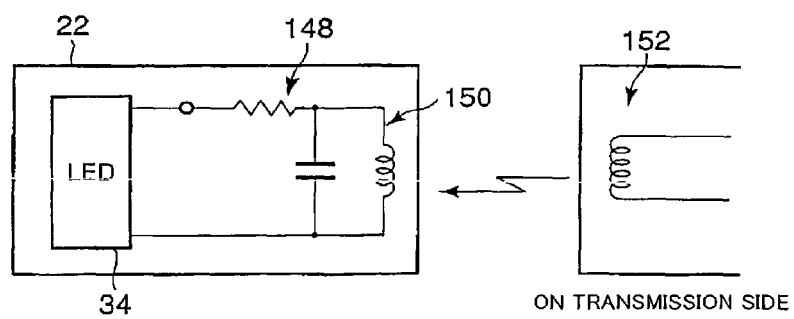
FIG. 13B is a schematic view illustrating an internal structure of a receiver case.

As shown in FIG. 13A, the receiver case 26 has an internal structure that generally includes a receiver means, a converter circuit 148, and a light-emitting element (LED) 34. As shown in FIG. 13B, the reception means includes a receiver coil 150. The receiver coil 150 is applied with a varying magnetic field by means of a transmission means (transmission coil) 152. Then, alternating current occurs in the receiver coil 150. The alternating current flows from the receiver coil 150 to the converter circuit 148, by which the alternating current, resulting from the receiver coil 150, is converted to a direct current. Therefore, the LED 34 emits a light in response to the direct current.

As shown in FIGS. 14A and 14B, formed in the inserter section 68 of the endoscope 66 used in the presently filed embodiment are first and second treatment implement insertion channels (not shown). FIG. 14A shows a layout of the distal end 68a of the inserter section 68. Formed on the distal end 68a are an objective lens 154, a pair of illumination lenses 156 and first and second forceps outlets 158a, 158b formed in communication with the first and second channels, respectively. As shown in FIG. 14B, the forceps 144 is disposed in the first channel in communication with the first forceps outlet 158a. Likewise, an endoscope clip device 160 is disposed in the second channel in communication with the second forceps outlet 158b.

Fourth Modification of Third Embodiment

Now, a modification of the third embodiment is described, in which reference is made to FIGS. 15A and 15B to describe operations of placing a loop-shaped light marker 130 on a lesion 100 using a lesion identification system for surgical system of the presently filed embodiment.

As shown in FIG. 14C, the loop-shaped light marker 130 is inserted to an internal site under a situation where the retainer 146 of the light source 22 is preliminarily gripped with the forceps 144 at an outside of the internal site and indwell in a position so as to surround a periphery of the lesion 100 as shown in FIG. 15A. Of course, in cases where an outer diameter of the loop-shaped light marker 130 is smaller than a diameter of the treatment implement insertion channel to be available for insertion, the loop-shaped light marker 130 may be inserted to the internal site through the forceps opening (not shown) while holding the loop-shaped light marker 130.

Upon keeping such a condition stated above, using the endoscope clip device 160, shown in FIG. 14B, allows the clips 160a to pinch the light guide 138 and the clips 160a are caused to engage the mucous membrane as shown in FIG. 15A. With the light guide 138 clipped with the plural clips 160a while the respective clips 160a are caused to engage the mucous membrane, the loop-shaped light marker 130 is fixed in place in a way to surround the lesion 100.

Under such a situation, the receiver coil 150 of the light source 22 applied with, for instance, a varying magnetic field using the transmitter coil 152, the LED 34 emits a light. The light emitted from the LED 34 is introduced from an end of the light guide 138 to the internal part of the light guide 138. The presence of a leakage of light introduced to the light guide 138 allows the light guide 138 to emit a light.

For instance, since the large intestine is formed of a thin tissue, the CCD element 58 of the rigidscope 14 is able to pick up the light, emitted from the light guide 138, together with a real image of an outer coat of the large intestine 300. Then, as shown in FIG. 15B, a loop-shaped position of the light, emitted from the light guide 138, is displayed together with the real image of the outer coat of the large intestine 300 over the monitor 80 via the image processor connected to the rigidscope 14.

Also, upon using the LED 34 that emits the light with the near-infrared range, it is possible to identify not only the lesion 100 present in the thin tissue such as the large intestine 300 but also the lesion 100 present in a tissue thicker than the large intestine 300 in the same way.

Fourth Embodiment

Now, reference is made to FIGS. 16A-16B to 18A-18B to describe a fourth embodiment.

Figure 16A:
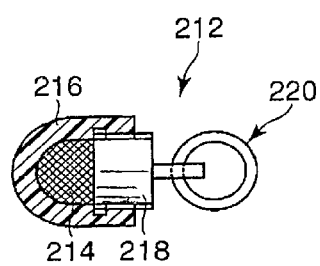
FIG. 16A is a schematic cross-sectional view of a fluorescent marker containing fluorescent substance for use in a lesion identification system for surgical operation of a fourth embodiment according to the present invention.

As shown in FIG. 16A, the fourth embodiment contemplates to use a fluorescent marker 212 as a light marker in place of the light markers (light source clips 12) described in conjunction with the first embodiment. The fluorescent marker 212 is comprised of a transparent capsule member 216 in which fluorescent substance (phosphor) is sealed, a cap 218 serving as a lid to close the capsule member 216, and a ring 220 connected to the cap 218. Examples of fluorescent material include, for instance, riboflavin (vitamin B2), thiamine (vitamin B1), NADH (nicotinamide adenine dinucleotide), FMN (flavin mononucleotide), and ICG (Indrocyanine Green).

Figure 16B:
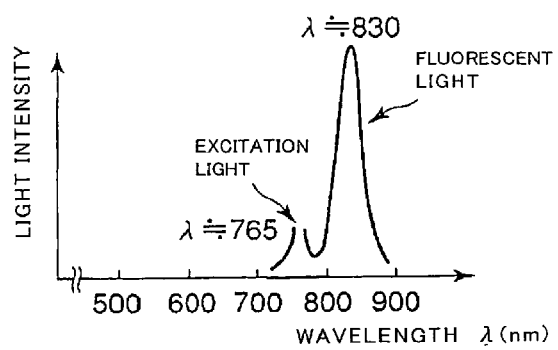
FIG. 16B is a graph illustrating a characteristic of a fluorescent light in terms of an excitation light radiated to fluorescent light.

FIG. 16B is a graph illustrating characteristics of an excitation light, needed for exciting ICG forming one of fluorescent material 214, and a fluorescent light of ICG excited by the excitation light in an overlapped relationship. In FIG. 16B, the coordinate indicates a light intensity and the abscissa indicates a wavelength $\lambda$ (nm). When the excitation light (light with a wavelength in a visible range) with a wavelength of approximately 765 nm is radiated to the ICG, the fluorescent light is emitted with a wavelength of about 830 nm.

Figure 17A:
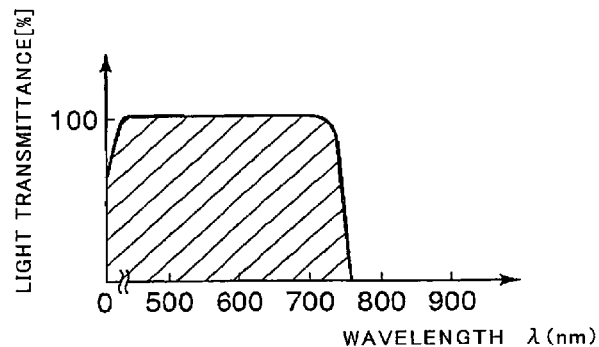
FIG. 17A is a graph illustrating a characteristic of a light source of an endoscope for use in the lesion identification system for surgical operation of the fourth embodiment.

FIG. 17A shows a characteristic of an illumination light introduced from the rigidscope 14. As shown in FIG. 17A, the illumination light of the rigidscope 14 involves a light with a wavelength of 765 nm needed for exciting ICG. For this reason, the light source of the rigidscope 14 used in general practice can be treated as an excitation light for the ICG forming the fluorescent material 214.

Figure 17B:
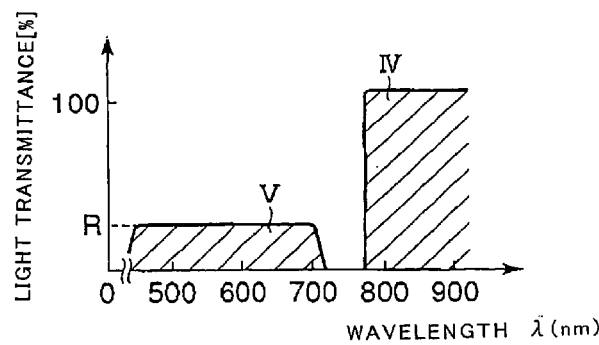
FIG. 17B is a graph showing a status in which characteristics of two filters, disposed in an adjustable filter section of a rigidscope, are superimposed.

FIG. 17B is a graph illustrating optical characteristics of the first and second optical filters (not shown) of the adjustable filter section 60 (see FIG. 3C) of the rigidscope 14 in an overlapped relationship. The first optical filter has a characteristic that transmits a light with a wavelength of, for instance, 380 to 730 nm. For this reason, the first optical filter is available to transmit a light with a wavelength in a substantially visible range.

The second optical filter has a characteristic that transmits a light with a wavelength of, for instance, a value exceeding 780 nm. For this reason, the second optical filter is available to transmit a light with a wavelength in a substantially near-infrared range. In this case, the adjustable filter section 60 is configured such that the second optical filter has a greater transmittance than that of the first optical filter.

Now, reference is made to FIG. 18 and description is made of operations of indwelling a fluorescent marker 212, caught by the clip 160a, in the lesion 100 using the lesion identification system for surgical operation of the presently filed embodiment. A region X in FIG. 18B designates a site inside a large intestine and a region Y indicates another site on an abdominal cavity. This similarly applies to FIGS. 23 and 24B.

As shown in FIG. 18A, the clip 160a is inserted through the treatment implement insertion channel 70 using the clipping device 160 with the ring 220 of the fluorescent marker 212 being caught by the clip 160a of the endoscope, and the clip 160a is caused to engage a mucous membrane of an organism to be indwelt in the vicinity of the lesion 100 as shown in FIG. 19B. This results in a condition where the fluorescent marker 212 is indwelt in the organism.

Upon radiating an illumination light (see FIG. 17A), including an excitation light from the light source (illuminating optical system) of the rigidscope 14, onto the fluorescent marker 212, fluorescent material 214 is excited to emit a fluorescent light. For this reason, if fluorescent material 214, such as ICG, is excited due to the light source of the rigidscope 14, a fluorescent light with a wavelength of 830 nm is released and selectively picked up by the CCD element 58 via the adjustable filter section 60 of the rigidscope 14 at an outside of the large intestine 300.

Thus, the presently filed embodiment is able to have operations and effects equivalent to those of the first embodiment set forth above. Particularly, the presently filed embodiment employs the fluorescent marker having fluorescent material that emits a fluorescent light upon receipt of an excitation light with a given wavelength. For this reason, by fixing the fluorescent marker onto a site close proximity to the lesion using the fixing means and using the endoscope to observe a fluorescent light resulting from the excitation light radiated onto fluorescent material of the fluorescent marker, the lesion in the organ can be identified in a position outside the organ where the lesion is present.

Further, the excitation light of the above fluorescent material includes a light to be emitted from the light source of the above endoscope. Therefore, no need arises for preparing a new light source, enabling the lesion to be identified in a simplified structure.

Furthermore, the above fluorescent material may preferably include substance that emits a light with at least a portion of a wavelength ranging from 780 nm to 1300 nm in response to the above excitation light. The fluorescent light with such a wavelength is easier to transmit through the organism than that of the wavelength less than such a range. Thus, the use of the light with such a portion of the wavelength allows the lesion to be more easily observed with the endoscope, providing the ease of identifying the lesion.

Fifth Embodiment

Now, a fifth embodiment is described with reference to FIGS. 19A-19B to 20A-20C. This embodiment is a modified form of the fourth embodiment and the same component parts as those of the fourth embodiment bear like reference numerals to omit detailed description.

The ring 220 of the fluorescent marker 212 shown in FIG. 19A is formed of rubber material that is flexible (elastically deformable) in a radial direction.

In the meanwhile, as shown in FIGS. 19B and 19C, a hood 24 is mounted onto the distal end 68a of the inserter section 68 of the endoscope 66 by which the fluorescent marker 212 is indwelt in the vicinity of the lesion 100. The hood 224 has a distal end a portion of which is formed with a cutout 226.

Disposed on an outer periphery of the hood 24 for sliding capability is a tubular element 228. When the tubular element 228 is caused to press the ring 220, made of rubber material, to allow the same to drop off from the hood 224, the ring 220 is removed from the outer periphery of the hood 224 to contract in diameter.

Next, reference is made to FIG. 20 to describe operations of indwelling the fluorescent marker 212 in the lesion 100 using the lesion identification system for surgical operation of the presently filed embodiment.

Figure 20A:
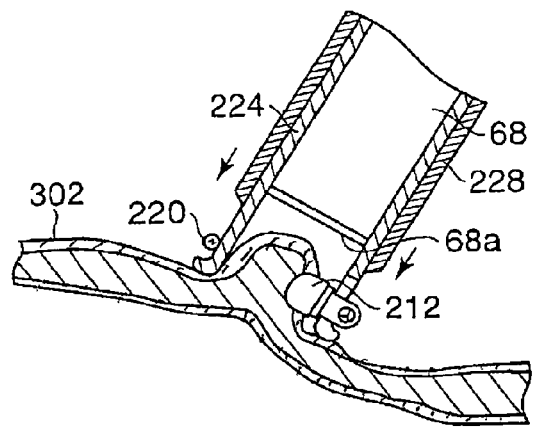
FIG. 20A is a schematic view showing a status wherein an organism is suctioned to an inside of the hood using a suctioning function of the endoscope of the lesion identification system for surgical operation of the fifth embodiment.
Figure 20B:
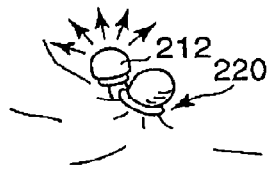
FIG. 20B is a schematic view illustrating a status wherein the ring is released with the organism suctioned while the ring is elastically deformed to bind the organism under which the fluorescent marker is indwelt in the organism.
Figure 20C:
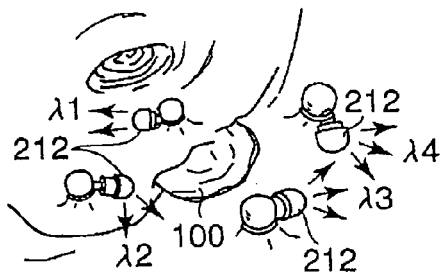
FIG. 20C is a schematic view illustrating a status in which a plurality of fluorescent markers, containing fluorescent substances with wavelengths different from each other, shown in FIG. 19B are indwelt around a lesion.

As shown in FIG. 20A, a mucous membrane 302 of an organism is suctioned with the distal end 68a of the inserter section 68 of the endoscope 66. Then, the mucous membrane 302 is caused to deform toward the distal end 68a of the inserter section 68 and suctioned into an interior of the hood 224. Under such a status, as the tubular element 228 is moved forward to remove the ring 220 from the outer periphery of the hood 224, the rubber ring 220 contracts in diameter due to elastic deformation to be brought into a condition where the rubber ring 220 binds the mucous membrane 302 at a site in the vicinity of the lesion 100 as shown in FIG. 19B. Similarly, the fluorescent markers 212, containing fluorescent substances 214 with different characteristics, are fitted to the sites around the lesion 100. Therefore, as the fluorescent substances 214 of the fluorescent markers 212 are excited to cause the fluorescent markers 212 to emit fluorescent lights with wavelengths of λ1, λ2, λ3, different from each other, a location of the lesion 100 can be recognized (identified) through the rigidscope 14.

Sixth Embodiment

Now, a sixth embodiment is described with reference to FIG. 21.

Figure 21:
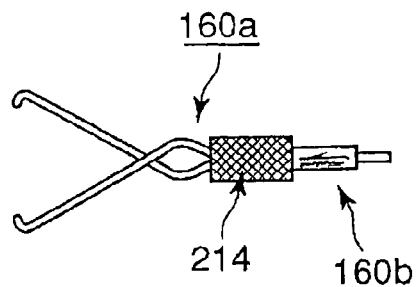
FIG. 21 is a schematic view of a clip, having a base coated with fluorescent material, for use in a lesion identification system for surgical operation of a sixth embodiment according to the present invention.

As shown in FIG. 21, a mixture of fluorescent substance 214 and resin powder is coated on an outer periphery of a base 160b of the clip 160a of the endoscope described in conjunction with the fourth embodiment. Thus, the clip 160a has a function as a fluorescent marker. Examples of resin may include polypropylene, polyethylene and polysulfon. Fluorescent substance may include the same constituents as those of fluorescent substance described with reference to the fourth embodiment. As described in connection with the fourth embodiment, fluorescent substance 214 is excited with, for instance, the light source of the rigidscope 14 to emit a fluorescent light with a given wavelength.

The clip 160a operates in the same manner as that of the fourth embodiment. Due to fluorescent substance 214 coated on the clip 160a per se, no need arises for advance preparation to entangle the fluorescent marker to the clip 160a like the embodiment shown in FIG. 18A, providing a remarkable ease in usage.

Seventh Embodiment

Next, a seventh embodiment is described with reference to FIG. 22. This embodiment is a modified form of the sixth embodiment and the same component parts as those used in the sixth embodiment bear like reference numerals to omit detailed description.

Figure 22:
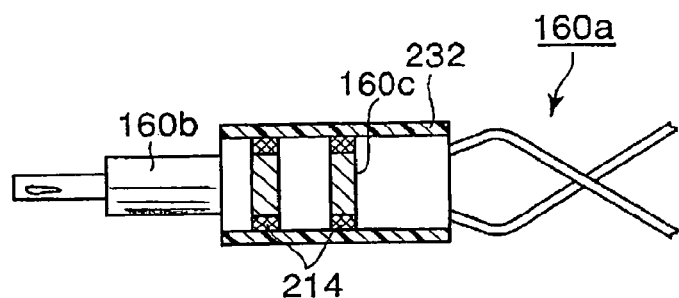
FIG. 22 is a schematic view of a clip having a base incorporating fluorescent material for use in a lesion identification system for surgical operation of a seventh embodiment according to the present invention.

As shown in FIG. 22, formed on the outer periphery of the base 160b of the endoscope clip 150a is, for instance, a plurality of recesses 160c. Filled in these recesses 160c is fluorescent substance 214. The base 160b under such a state is covered with a transparent heat shrinkable tube 232. The heat shrinkable tube 232 is a tube that is caused to shrink upon application of heat at a given temperature. Therefore, fluorescent substance 214 is sealed in the recesses 160c with the heat shrinkable tube 232.

The clip 160a, serving as the fluorescent marker, operates in the same manner as that of the sixth embodiment. Due to fluorescent substance 214 disposed in the clip 160a per se, there is no need for advance preparation to entangle the fluorescent marker to the clip 160a, providing a remarkable ease in usage.

Eighth Embodiment

Now, an eighth embodiment is described with reference to FIG. 23.

Figure 23:
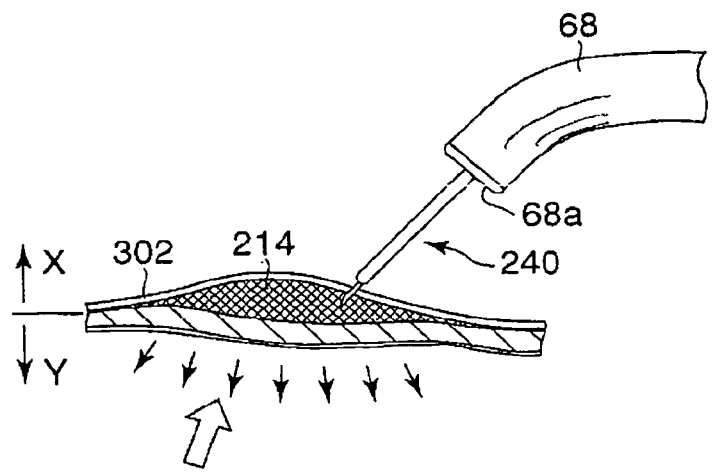
FIG. 23 is a schematic view illustrating a status wherein fluorescent material with a viscosity is injected to a mucous membrane of an organism using a regional injection needle in a lesion identification system for surgical operation of an eighth embodiment according to the present invention.

As shown in FIG. 23, fluorescent substance 214 is mixed with organism-adapted substance, such as hyaluronate sodium that is viscous substance, into liquid, which in turn is injected to a site underneath a mucous membrane 302 in the vicinity of the lesion 100 using a regional injection needle 240 under monitored conditions through the use of the flexible-scope 68. Under such a condition, fluorescent substance 214 is excited using the light source of the rigidscope 14 and the resulting fluorescent light, emitted from fluorescent substance 214, is picked up by the CCD element 58 of the rigidscope 14. Other operational procedures are similar to those of the fourth embodiment.

Ninth Embodiment

Figure 24A:
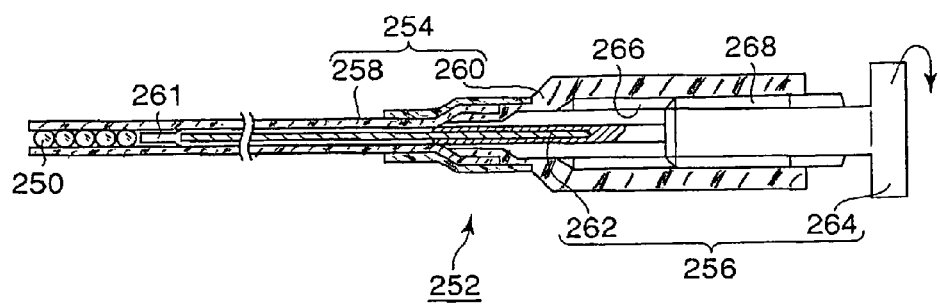
FIG. 24A is a schematic cross-sectional view illustrating an applicator for fluorescent balls, in each of which fluorescent material is filled, for use a lesion identification system for surgical operation of a ninth embodiment according to the present invention.
Figure 24B:
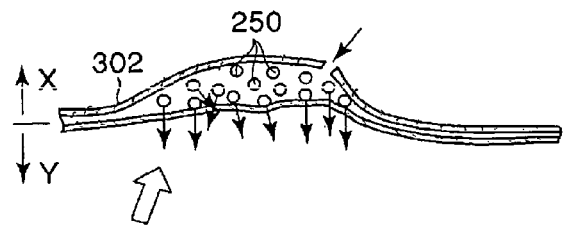
FIG. 24B is a schematic view illustrating a status in which a mucous membrane is partially incised and fluorescent balls are injected to an inside of the mucous membrane.

Now, a ninth embodiment is described with reference to FIGS. 24A and 24B

With the presently filed embodiment, in place of implementing the process to inject liquid, containing fluorescent substance 214 mixed with hyaluronate sodium, into the mucous membrane 302 using the regional injection needle 240 described in connection with the eighth embodiment, the mucous membrane 302 of the organism is partially incised and beady fluorescent balls 250, in each of which fluorescent substance 214 is sealed, are introduced to a site underneath the mucous membrane using a fluorescent ball applicator 252. Under such a condition, fluorescent lights are excited in the same manner as that described in connection with the eighth embodiment.

The fluorescent ball applicator 252, which is introduced to the mucous membrane underneath of the organism, is comprised of a tubular member 254 and a pusher 256. The tubular member 254 includes a flexible tube 258 with a diameter available to be inserted to the treatment implement insertion channel 70 of the endoscope 66, and a grip 260 located on a base of the flexible tube 258. The flexible tube 258 has a distal end whose inner peripheral surface is formed with a corrugated shape in match with a size of each fluorescent ball 250. The pusher 256 is comprised of a flexible wire 262 having flexibility, and a rotatable member 264 connected to a base of the flexible wire 262.

The grip 260 has an inner peripheral wall formed with a female threaded portion 266. Formed on an outer periphery of the rotatable member 264 is a male threaded portion 268, which is screwed into the female threaded portion 266. Thus, as the rotatable member 264 is rotated, the rotatable member 264 is moved forward or rearward to allow the fluorescent balls 250 to drop off from a distal end of the flexible tube 258.

With such a structure, a part of, for instance, the mucous membrane 302 of the organism is incised and the fluorescent balls 250 are introduced to the mucous membrane underneath. Then, the fluorescent balls 250 have the same function as that described in connection with the eighth embodiment.

Also, the fluorescent balls 250 may be caused to adhere to the lesion 100 using adhesive, resulting in the same operations and effects as those obtained described above.

While the present invention has heretofore been described above in connection with various embodiments with reference to the accompanying drawings, the present invention is not limited to such embodiments described above and involves all of implementations that can be practiced without departing from the spirit and scope of the present invention.

What is claimed is:

1. A method of identifying a lesion which is present inside a tubular organ of a patient for surgical operation, the method comprising the steps of:
   delivering, using applicator, a light marker into a tubular organ of a body of a patient through a natural opening of the patient and introducing, from inside a tubular wall of the tubular organ, the light marker to a site underneath a mucous membrane, the site being formed by partially incising the mucous membrane of the tubular wall from inside the tubular organ within the body, the site being in the vicinity of the lesion, the introduced light marker being indwelt in the vicinity of the lesion of the tubular organ, wherein the light marker is composed of a plurality of beady fluorescent balls formed to emit light whose wavelengths belong, at least partly, to a range of wavelengths of near-infrared range; and
   inserting an endoscope into the body of the patient and locating a tip of the endoscope outside the tubular organ within the body, the tip of the endoscope facing the lesion via the wall of the tubular organ;
   making the endoscope radiate visible light toward the wall of the tubular organ from outside the wall;
   picking up, using the endoscope, an image which is based on both reflected light of the light radiated from the endoscope and the light emitted from the fluorescent substance of the indwelt light marker and transmitted through the wall at an outside position of the wall of the tubular organ; and
   identifying a location of the indwelt light marker based on a position of the light on the image by processing both the visible reflected light and the light emitted from the fluorescent substance of the indwelt light marker into two types of image signals, respectively, and displaying on a monitor the two types of image signals as an image in which an image processed based on one of the two types of image signals processed with the light emitted from the fluorescent substance of the indwelt light marker is superposed on an image processed based on the other of the two types of image signals processed with the visible reflected light, the indwelt light marker positionally indicating an area of the tubular organ in which the lesion is present.

2. The method of claim 1, wherein
   the beady fluorescent balls each containing the fluorescent substance and emitting the light.

3. The method of claim 1, wherein the applicator contains therein the beady fluorescent balls beforehand and discharging the beady fluorescent balls at the site.

4. The method of claim 1, comprising a step of excising, after the surgical operation, the lesion of the tubular organ together with the indwelt light marker.

5. The method of claim 4, wherein the delivering step includes a step of forming the site by partially incising the mucous membrane of the wall of the tubular organ from inside the tubular organ within the body before delivering the light marker to the site.

6. The method of claim 1, wherein the delivering step includes a step of forming the site by partially incising the mucous membrane of the wall of the tubular organ from inside the tubular organ within the body before delivering the light marker to the site.

* * * * *